United States Patent [19]

Purzycki et al.

[11] Patent Number: 4,963,179
[45] Date of Patent: Oct. 16, 1990

[54] PRESERVATIVES CONTAINING β-BROMO-β-NITROSTYRENE FOR USE IN AQUEOUS SYSTEMS

[75] Inventors: Kenneth L. Purzycki, Lake Parsippany; Joseph A. Virgilio, Wayne, both of N.J.

[73] Assignee: Givaudan Corporation, Clifton, N.J.

[21] Appl. No.: 244,773

[22] Filed: Sep. 14, 1988

[51] Int. Cl.$^5$ .................... A01N 25/10; A01N 25/12; A01N 29/10
[52] U.S. Cl. .................................. 71/67; 71/DIG. 1; 514/741
[58] Field of Search .............. 71/67, DIG. 1; 514/741

[56] References Cited

U.S. PATENT DOCUMENTS

| | | | |
|---|---|---|---|
| 2,876,160 | 3/1959 | Schoch et al. | 514/725 |
| 3,535,423 | 10/1970 | Ordas | 71/DIG. 1 |
| 3,629,465 | 12/1971 | Manowitz et al. | 514/741 |
| 3,871,860 | 3/1975 | Manowitz et al. | 71/67 |
| 4,755,397 | 7/1988 | Eden et al. | 71/DIG. 1 |

OTHER PUBLICATIONS

"Kirk–Othmer, Encyclopedia of Chemical Technology", vol. 22, John Wiley and Sons, Inc., N.Y., 1983, pp. 510–513.

EPA, "Inert Ingredients in Pesticide Products; Policy Statement", Federal Register, vol. 52, No. 77, (1987), 13305–13309.

Brochure of the A. E. Staley Manufacturing division of Staley Continental, Inc., Decatur, Ill., describing Micropor Buds® dated 2/88.

*Primary Examiner*—Richard L. Raymond
*Assistant Examiner*—K. L. Konstas
*Attorney, Agent, or Firm*—Robert F. Tavares; Linda A. Vag

[57] ABSTRACT

The use of a novel system for preserving aqueous systems normally subject to spoilage is disclosed. The system comprises the incorporation of β-bromo-β-nitrostyrene onto a solid maltodextrin or corn syrup solid of low to intermediate dextrose equivalency.

6 Claims, No Drawings

PRESERVATIVES CONTAINING β-BROMO-β-NITROSTYRENE FOR USE IN AQUEOUS SYSTEMS

BACKGROUND OF THE INVENTION

The present invention relates to processes and compositions for preserving aqueous systems against the deleterious action of bacteria, fungi and algae.

It is well known that various aqueous systems containing metabolizable components, either in trace or major quantities, are normally susceptible to attack and degradation by microorganisms. Examples of such compositions are cutting oils, cosmetics such as lotions and creams, fuel oil, textile emulsions, latex emulsions and paints, starch-base adhesives, industrial cooling water, emulsion waxes, water used in pulp and paper manufacture (so-called "process" water, e.g., "white water"), and flood water used in secondary oil recovery methods.

A number of problems and limitations have recently faced those in the art who seek to provide effective antimicrobial preservatives for such aqueous systems. These problems involve concerns about worker exposure and environmental impact. Many preservatives are effective because they are toxic to the microorganisms at low concentrations, i.e. concentrations in the order of about 100 parts per million. Human exposure to such preservatives in the part per million range does not normally pose a risk that raises concern. The pure product, however, may pose an unacceptable risk to workers who may be exposed to the pure concentrated material on a daily basis and who must protect themselves from accidental inhalation or accidental exposure to the skin. In the case where the substance is a liquid, its vapor pressure may be of concern, if concentrations in the air could reach levels which could be harmful to workers. If the material is a solid or a powder the inhalation of dust becomes a concern.

One way to keep the concentration of such antimicrobial agents to an acceptable handling level is to use diluents or inert carriers. Such diluents or carriers are also desirable in order to assist in delivering the antimicrobial agents to the medium to be preserved. These diluents must, of course, meet certain criteria. They must be compatible with a particular antimicrobial agent and with the medium in which the antimicrobial agent is to be used. They shouuld not be highly flammable and should not be toxic. Very few diluents can satisfy these criteria at an acceptable price.

More recently, pressures concerning the toxicity of the diluent and its compatability with the environment have served to restrict the number of diluents that are acceptable. It is expected that even fewer diluents or carriers will be acceptable in the future.

There is a need in the industry to find a diluent or a carrier system which meets the following criteria:

(1) The diluent or carrier must be compatible with the antimicrobial agent and should not diminish or destroy the antimicrobial activity.

(2) The final product must have a flash point of greater than 120 degress Fahrenheit in order to avoid dangers due to flammability.

(3) The system must work in the medium for which it is intended.

(4) It should not be on list 1 or list 2 of the Environmental Protection Agency's "Inert Ingredients in Pesticide Products; Policy Statement". (Federal Register, volume 52, number 77, dated April 22, 1987. Lists 1 and 2 cover inert ingredients of toxicological concern and potential toxicological concern, respectively.)

(5) The system must be economically competitive, i.e., it must not be so expensive that the system cannot compete in the market place.

(6) The diluent or carrier should be odorless, or at least have a pleasant odor.

SUMMARY OF THE INVENTION

The invention provides a novel means for the saft handling of β-bromo-β-nitrostyrene which meets the criteria set forth above, and which minimizes human exposure and environmental concerns. The present invention provides a product which comprises β-bromo-β-nitrostyrene absorbed into or encapsulated into a biodegradable and relatively inert, partially hydrolyzed starch such as a maltodextrin or corn syrup solid. Hydrolyzed starches are relatively inert to most antimicrobial agents and usually result in a product with a high flash point, in most cases greater than 200 degrees Fahrenheit. The hydrolyzed starch does not contribute any odor to the final product. It is water soluble and therefore releases the active ingredients in aqueous systems. It is biodegradable and a natural food material, which is not only compatible with eco-systems but actually contributes to them in a positive fashion. The fact that the final product is a solid minimizes worker and user exposure and environmental contamination from spills.

The invention also provides a process for the manufacture of said product. A suitable maltodextrin or corn syrup solid can be mixed with a solution of β-bromo-β-nitrostyrene in the desired proportions. The solvent can then be removed, for example, by vacuum distillation.

DESCRIPTION OF THE PREFERRED EMBODIMENTS

Partially hydrolyzed starches containing dextrose, maltose and higher molecular weight saccharides are available from corn starch. The hydrolyzed starch products are usually defined on the basis of their reducing sugar content referred to as the dextrose equivalency (DE). Solid, partially hydrolyzed starches with a dextrose equivalent (DE) of between 1 and 20 are preferred in the practice of the present invention. Partially hydrolyzed starches with a DE of less than 20 are generally classified as maltodextrins and are normally solid compositions of varing particle size and densities. Suitable solid hydrolyzed starches are available under such tradenames as Amaizo Fro-Dex ® (American Maize-Products Co.), Maltrin ® (Grain Processing Corporation) and Micropor Buds ® (A. E. Staley Manufacturing Company). The source of the maltodextrin is not critical to the practice of the present invention. Micropor Buds ® 1005, 1015 and 2010, with DE values of 10, 10 and 20, respectively, have been used for purposes of illustrating the present invention but any solid hydrolyzed starch with a DE of between 1-20 may be used. Maltodexrins with a DE value of 5-15 are preferred since they are more readily available and more economical to use.

In preparing the novel systems of the invention, it is preferred to first dissolve the β-bromo-β-nitrostyrene in a non-aqueous solvent. The nature of the solvent is not critical other than that it should be compatible with the antimicrobial agent, should be one which will dissolve the antimicrobial agent and should not react with the partially hydrolyzed starch. Suitable solvents for most applications would be, for example, hydrocarbon solvents such as toluene and the like.

The solution containing the antimicrobial agent and a suitable partially hydrolyzed starch are mixed together in the proper proportions to yield a final product with a correct level of antimicrobial agent. For example, if a final product is desired to have 50% partially hydrolyzed starch and 50% β-bromo-β-nitrostyrene, one could suitably add 100 parts of the partially hydrolyzed starch to 400 parts of a 25% solution of β-bromo-β-nitrostyrene and a suitable solvent, mix for a period of time and then remove the solvent under reduced pressure. The final product is a granular, free-flowing solid. Under most circumstances, one can vary the ratio of the antimicrobial agent to the partially hydrolyzed starch from as little as 0.5% antimicrobial agent and 99.5% partially hydrolyzed starch to as high as 90% antimicrobial agent to 10% partially hydrolyzed starch. It is preferred, however, to use a ratio of from 40–60% β-bromo-β-nitrostyrene to 60–40% partially hydrolyzed starch, since this provides the best free-flowing solid. The most preferred ratios will depend on a number of factors including the use to which the antimicrobial agent is to be applied.

Compositions prepared according to the present invention were found to be stable over time. Analysis of compositions containing 25% and 50% β-bromo-β-nitrostyrene on maltodextrin (DE=10), using standard Ultraviolet Spectroscopic methods, showed no deviation in the composition of the mixtures after 30 days of storage.

The compositions have also been shown to be effective, in general, against a broad spectrum of microorganisms which attack the aqueous systems described herein. Samples of 25% and 50% β-bromo-β-nitrostyrene on maltodextrin were evaluated in agar to obtain a minimum inhibitory concentration range of each sample against a series of bacteria, yeast, and molds. Pure β-bromo-β-nitrostyrene served as a control. The test was designed with small dilution increments so that relatively minor differences in antimicrobial activity could be detected. Results indicate that the activity of the two β-bromo-β-nitrostyrene/maltodextrin samples compared favorably with the control. No significant differences in antimicrobial activity were detected. In the ranges presented in the examples below, no growth occurred at the higher concentration while the lower concentration was non-inhibitory. (Maltodextrin was tested alone and was found to be non-inhibitory against all microorganisms at 100 mcg/ml, the highest concentration of carrier tested.)

The microbial activity of β-bromo-β-nitrostyrene diluted with maltodextrin is identical to an equivalent amount of the pure material, and would therefore be useful as a preservative of aqueous systems as described in U.S. Pat. No. 3,629,465.

ILLUSTRATION OF THE PREFERRED EMBODIMENTS

Example 1: Preparation of Product

To 400 grams of a solution consisting of 100 grams of β-bromo-β-nitrostyrene and 300 grams of toluene, is added 100 grams of a hydrolyzed starch with a DE of 10 available under the tradename Micropor Buds® (grade 1015). The resulting mixture is heated to a temperature of 50° C. The toluene is then removed under reduced pressure (30 mm Hg) at 50° C. to yield a granular solid. Analysis of the granular solid by Ultraviolet Spectroscopic analysis (UV) shows 48–52% β-bromo-β-nitrostyrene. (The range is due to deviations in the test procedure.)

Substitution of Micropor Buds® 1005 or 2010 for the Micropor Buds® 1015 in the above procedure yields the respective product containing 48–52% β-bromo-β-nitrostyrene.

Products containg 25% β-bromo-β-nitrostyrene are prepared using 350 grams of a solution of 50 grams of β-bromo-β-nitrostyrene in 300 grams of toluene in the above procedure. It is well within the skill of one in the art to determine the proper proportions necessary to prepare a product with the desired level of β-bromo-β-nitrostyrene.

Example 2: Microbial Activity

Samples of 25% and 50% β-bromo-β-nitrostyrene on Micropor Buds® grade 1015 were evaluated in agar to obtain a minimum inhibitory concentration range based on BNS concentration of each sample against a series of bacteria, yeast, and molds. Pure β-bromo-β-nitrostyrene served as a control. The test was designed with small dilution increments so that relatively minor differences in antimicrobial activity could be detected.

Results listed in the following tables indicate that the activity of the two samples compared favorably with the control. No significant differences in antimicrobial activity were detected.

Sample Identificaiton:

25 BNS 25% β-bromo-β-nitrostyrene/75% Micropor Buds® #1015
50 BNS 50% β-bromo-β-nitrostyrene/50% Micropor Buds® #1015
Control Pure β-bromo-β-nitrostyrene (m.p. 62°–63° C.)

TABLE I

BACTERIA
Minimum Inhibitory Concentration Range in mcg/ml

| Sample | Staphylococcus aureus | Escherichia coli | Pseudomonas aeruginosa | Proteus vulgaris | Babillus subtilis |
| --- | --- | --- | --- | --- | --- |
| 25BNS | >25 | 17.5–20.0 | 12.5–15.0 | 17.5–20.0 | 22.5–25.0 |
| 50BNS | >25 | 15.0–17.5 | 10.0–12.5 | 15.0–17.5 | 20.0–22.5 |
| Pure BNS | >25 | 15.0–17.5 | 10.0–12.5 | 15.0–17.5 | 20.0–22.5 |

TABLE II

| | YEAST, MOLDS | | | | |
|---|---|---|---|---|---|
| | Minmum Inhibitory Concentration Range in mcg/ml | | | | |
| Sample | Candida albicans | Aspergillus niger | Aspergillus oryzae | Penicillium piscarium | Aureobasidium pullulans |
| 25BNS | 15.0–17.5 | 7.5–10.0 | 17.5–20.0 | 7.5–10.0 | 2.5–5.0 |
| 50BNS | 12.5–15.0 | 7.5–10.0 | 15.0–17.5 | 7.5–10.0 | 2.5–5.0 |
| Pure BNS | 12.5–15.0 | 10.0–12.5 | 17.5–20.0 | 7.5–10.0 | 2.5–5.0 |

In the ranges presented, no growth occurred at the higher BNS concentration while the lower BNS concentration was non-inhibitory. Micropor Buds ® alone was non-inhibitory against all microorganisms at 100 mcg/ml, the highest concentration of carrier tested.

Example 3: Stability and Compatability

Samples of 25% and 50% β-bromo-β-nitrostyrene on Micropor Buds ® grade 1015 were placed in brown sealed bottles and assayed for β-bromo-β-nitrostyrene by standard Ultraviolet Spectroscopic methods over 30 days period.

TA8LE III

| β-bromo-β-nitrostyrene (BNS)/Micropor Buds ® Stability | | | |
|---|---|---|---|
| | Percent β-bromo-β-nitrostyrene | | |
| Sample | Initial | 14 days | 30 days |
| 25% BNS | 24.7 | 24.1 | 24.5 |
| 50% BNS | 51.2 | 51.2 | 50.6 |

We claim:

1. An antimicrobial composition which comprises an effective amount of β-bromo-β-nitrostyrene absorbed on a partially hydrolyzed starch with a DE value of 20 or less.

2. A composition according to claim 1 consisting essentially of 90–10% β-bromo-β-nitrostyrene and 10–90% of partially hydrolyzed starch.

3. A composition according to claim 2 consisting essentially of 50–25% β-bromo-β-nitrostyrene and 50–75% partially hydrolyzed starch.

4. A composition according to claim 3 wherein the DE value is from 5 to 15.

5. A process for combatting spoilage caused by the action of microorganisms in aqueous emulsion compositions normally subject to such spoilage, which comprises inhibiting said organism in such compositions with an effective inhibiting amount of a composition which comprises β-bromo-β-nitrosytrene absorbed on a partially hydrolyzed starch with a DE value of 20 or less.

6. A process for combatting spoilage by the action of slime-forming algae, bacterial and fungi microorganisms in industrial cooling water and water used in pulp and paper manufacturing, which comprises inhibiting said slime-forming organism in such waters with an effective inhibiting amount of a composition which comprises β-bromo-β-nitrosytrene absorbed on a partially hydrolyzed starch with a DE value of 20 or less.

* * * * *